(12) United States Patent
Shaw

(10) Patent No.: US 6,474,472 B1
(45) Date of Patent: Nov. 5, 2002

(54) SAFETY SHARPS BAGGING APPARATUS

(75) Inventor: Thomas J. Shaw, Little Elm, TX (US)

(73) Assignee: Retractable Technologies, Inc., Little Elm, TX (US)

( * ) Notice: Subject to any disclaimer, the term of this patent is extended or adjusted under 35 U.S.C. 154(b) by 0 days.

(21) Appl. No.: 09/291,826

(22) Filed: Apr. 14, 1999

(51) Int. Cl.$^7$ .............................................. B65D 83/10
(52) U.S. Cl. ..................... 206/366; 206/370; 206/438; 220/908.3
(58) Field of Search ................................ 206/365, 366, 206/367, 370, 438; 220/495.05, 908.3

(56) References Cited

U.S. PATENT DOCUMENTS

| | | | |
|---|---|---|---|
| 2,666,967 A | | 1/1954 | Poitras |
| 4,466,538 A | | 8/1984 | Gianni |
| 4,494,652 A | * | 1/1985 | Nelson et al. ............... 206/370 |
| 4,890,734 A | | 1/1990 | Gach |
| 5,057,656 A | | 10/1991 | Galber |
| 5,097,950 A | * | 3/1992 | Weiss et al. ................. 206/370 |
| 5,259,501 A | * | 11/1993 | Withers et al. .............. 206/370 |
| 5,271,500 A | | 12/1993 | Szacon |
| 5,273,161 A | * | 12/1993 | Sagstetter ................... 206/366 |
| 5,947,950 A | * | 9/1999 | Shillington et al. ......... 206/370 |

* cited by examiner

Primary Examiner—Mickey Yu
Assistant Examiner—Jila Mohandesi
(74) Attorney, Agent, or Firm—Locke Liddell & Sapp LLP; Monty L. Ross

(57) ABSTRACT

A sharps bagging apparatus has an access member with one or more conforming openings which conform to the profile of a retracted medical device to allow bagging collected retracted medical devices with a satisfactory degree of assurance that all or virtually all the devices are in the safe retracted condition. The access member is used with a collapsible disposal bag which may removably fill a disposal container or in one embodiment be fixedly secured to the access member. The access member is adapted to fit plastic or wire containers removably or lockedly. Sloping sides in the access member create a centering well which tends to center a retracted device and may include a triggering wall which can activate the retraction mechanism of an unretracted device. When the access member is provided with an attached collapsible bag, they can be stacked for economical transport and storage.

31 Claims, 10 Drawing Sheets

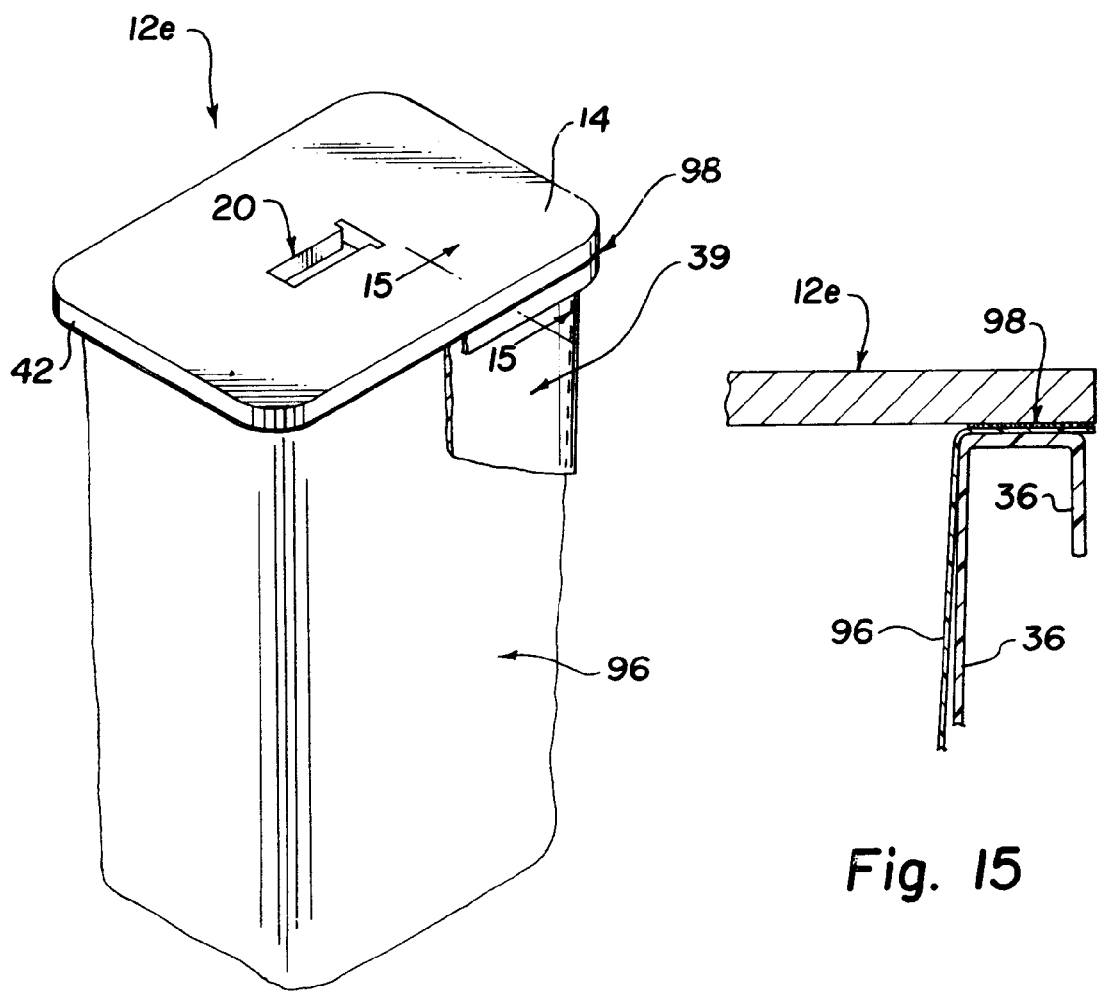
Fig. 14
Fig. 15
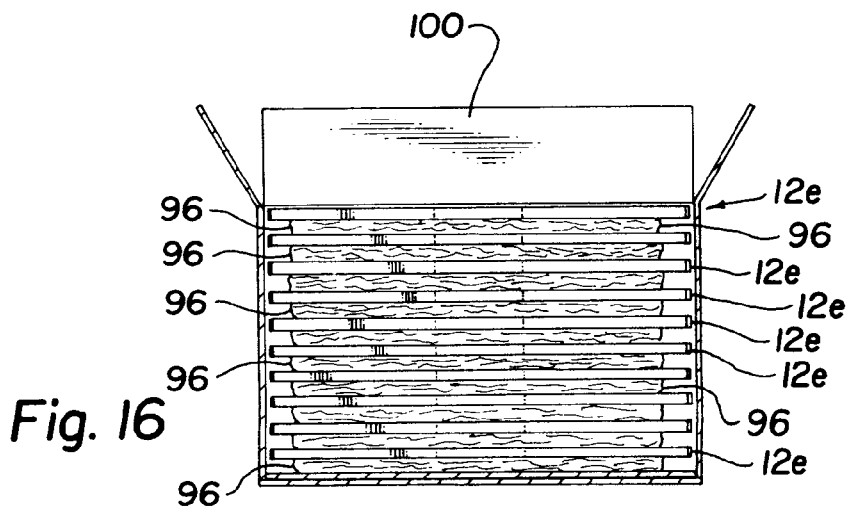
Fig. 16

SAFETY SHARPS BAGGING APPARATUS

BACKGROUND OF THE INVENTION

1. Field of the Invention

The invention pertains to safe disposal of medical sharps devices which exist in a safe and an unsafe state.

2. Background of the Art

Hospitals, doctors offices and laboratories are faced with the prospect of safely handling and disposing of needle-bearing and blade-bearing medical devices which are contaminated with blood or body fluids containing infectious agents. Medical facilities typically dispose of such medical devices in what are called "sharps" containers or boxes. These are typically hard sided plastic boxes with an opening in the top through which used medical devices are deposited after use. The sides must be puncture proof and are well known in the art. Standard sharps containers must meet regulations to make sure needles do not inadvertently become exposed to pose a danger to housekeeping staff and disposal personnel.

Because of the extreme hazard posed by used medical devices of this kind, the disposal process requires removal of the sharps containers from the hospital rooms and transport to an incinerator where the entire container and contents are incinerated. Since many of these containers cost approximately $4 to $12 at the present time, there is a significant cost associated with incineration as well as the creation of unnecessary air pollution hazards.

Because of the rise and prevalence of incurable infectious viral diseases, there has been a development of single use retractable medical devices including syringes, catheter introducers, intravenous needles and blood collection tube holders. Devices such as these have a needle, and a retraction activation structure which may vary somewhat between devices. In the better syringes, this involves merely a continuation of the pushing motion, for example, as fluid is injected to complete the activation of the retraction mechanism. In the case of catheter introducers there may be wing like arms that are squeezed to release a retractable needle into the housing. There are also devices having a safety shield that is pulled out over the needle to make it safe and devices where the needle is pulled back into the body of the device to make it safe. This latter type of device may also have a breaking part which is removed after the needle is safely within the body of the device.

There would be a significant cost savings and reduction in waste if it were possible to confidently bag used retracted medical devices for disposal in the manner of soft medical waste. Soft medical waste is normally bagged in red plastic bags similar in nature to a common plastic trash bag, which costs far less than $1.00 per bag. Heretofore, using flexible plastic bags instead of hard sided sharps containers has not been considered practical even for retractable needle devices because of the possibility that some unretracted medical devices might inadvertently be placed into the bag.

SUMMARY OF THE INVENTION

The invention provides an apparatus for removing the final small degree of uncertainty that may remain when the medical devices having a safe needle position, usually retractable medical devices, are being used exclusively. Disposal by bagging is now possible instead of incineration of a whole sharps container. It is far more economical and environmentally friendly to incinerate bagged medical needle devices than to dispose of needle bearing devices by incineration of relatively expensive sharps containers, as is done now.

A special access member is provided for use with disposal containers for sharps in a health clinic, doctor's office, hospital or laboratory. The access member is adapted for use with a disposal container for sharps and an impervious collapsible bag, preferably a plastic bag, is positioned to receive and collect medical devices in their safe condition. The access member has a conforming opening therein which conforms to the profile of a medical device in its safe condition. The walls of the conforming opening follow the exterior configuration of the medical device which has a protected needle. The access member is used in combination with the disposal bag for collecting medical devices in the safe condition of the needle which pass through the conforming opening. The invention deals with needle bearing medical devices which have a safe condition and an unsafe condition. The unsafe condition is the condition of the device in which the needle is exposed for use. In some devices which have a triggering mechanism, the unsafe condition might be called the "armed" condition which exists prior to activating the triggering mechanism to retract the needle into a housing or barrel. The safe condition is when the needle is "protected" so that is cannot inadvertently or otherwise cause a "needle stick". The safe condition may result from triggering the device to retract the needle. In some devices a separate needle assembly is physically attached to a movable member and pulled into the housing or barrel. The movable member may then have an extending portion which is broken off to prevent reuse. Other medical devices have a shield which slides with respect to the body of the device. After the needle is used, the slide is pulled out to cover the needle which remains in place. When the needle is covered so that it cannot penetrate a person's skin, the device is in the safe condition. When the needle is exposed for use, the device is in the unsafe condition. This is the context in which the safe or unsafe condition of a medical device should be understood with respect to the invention. The medical device may be referred to as "unsafe" or "safe" to indicate respectively that the needle is exposed for use or protected (covered) by means of some safety device that is provided with the medical device to convert the medical device to a safe condition of the needle.

The invention takes advantage of the fact that needle bearing medical devices in their unsafe condition with the needle exposed have a different profile than the same medical device has in its safe condition. Most of the examples herein deal with "self-retracting" syringes wherein an action by the user at the completion of use of the device triggers retraction of the needle, thus altering the geometry of the exterior of the device from that of its previous unsafe condition. Because the needle is no longer extended when converted to the safe condition, the profile is smaller. Other devices are contemplated by the invention where the profile is different by being larger in some places and smaller elsewhere. Such an example is the Safety Shield® device sold by Becton Dickenson. It has a fixed needle with a cylindrical shield which is pulled out over the needle. This action puts it in a safe condition while changing the geometry and thus the profile. In this case, the device may be lengthened because the sliding shield must be longer than the needle.

The access member is supported upon a sharps container or a plastic container which holds a removable preferably plastic bag. The access member may rest on the upper surface, may clip on, may be hinged to a container, may overlap the outer edges or may sit on an internal ledge in the open upper end of a sharps container. The access member may have a configuration which removably locks onto the upper edge of the container over an intervening layer of the bag material. In an alternate embodiment, the flexible disposable bag is secured to the access member so that the access member and collapsible bag can be handled together as a unit and can be conveniently collapsed for shipping and storage. In this alternate embodiment, the access member is disposed of with the bag.

The access member may have a single conforming opening or a plurality of conforming openings depending upon the usage of retractable devices in a particular facility. Powerful physiological satisfactions and a physical reminder is provided to the person using the devices. They are conditioned to insert the appropriate device in the appropriate conforming opening which matches its shape. The invention serves an important training function and provides physical and psychological reinforcement for the necessity for putting any medical device in the safe condition before disposal.

A safety shield is optionally provided on the undersurface of the access member to reduce the possibility that an unsafe medical device can be forced through the conforming opening. In particular, the conforming openings are considered to have a back end and a front end conforming to the device in question, and the safety shield includes depending barrier walls on the underside at each end of the opening which prevent longitudinal movement of the medical device in the axial longitudinal direction. With these barriers in place, no amount of cocking or tilting of the device will allow an unsafe device to pass through its conforming opening. The safety shield preferably includes a shelf mounted spaced below the conforming opening onto which safe devices fall. The safety shield includes a slot or opening that prevents radial extensions from inhibiting rolling of the medical devices on the tilted shelf and out the exit opening into the disposal bag.

An embodiment includes a access member having sloping surfaces leading to a conforming opening to create a centering well which tends to cause a safe medical device with a conforming profile to automatically center itself in relation to the conforming opening. In addition, the conforming opening may have a back end portion with a pressing wall extending above the opening which presses an activation structure of a medical device which has not been put in a safe condition of the needle. In the case of the retractable syringe, this may be a thumb cap on the back of the plunger which is not fully pressed forward to cause the retraction to take place. By pressing such a device into the opening having the pressing wall, a final opportunity for retraction is provided. An upstanding needle guard may be provided also to protect a user in the event they try to push an unsafe device through the opening.

A universal access member is provided with one or more openings for inserts which themselves contain the conforming opening or a plurality of conforming openings. Normally the inserts would contain only a single conforming opening so that a standard access member can be provided to accommodate inserts having openings of different shape. The user can also obtain several inserts and revert to a different insert as the need arises. Except in the case of the access member which has the collapsible bag attached, the access member is removed from the sharps container and reused while the bag with collected medical devices is taken to the incinerator. The access member and sharps container may have cooperating edge portions which serve to removably hold the access member in position. A one-way barrier may be included in the vicinity of the opening so that upsetting of the assembly will not result in escape of any of the collected syringes.

Use of the apparatus provides nearly complete assure, barring sabotage, that syringes which are collected in the disposal bag are truly retracted. Since the probability of collecting an unsafe syringe or other device is significantly reduced, disposal of retracted syringes by bagging is now a viable alternative.

BRIEF DESCRIPTION OF THE DRAWINGS

FIG. 14 is a cutaway perspective view of a access member having a conforming opening in combination with a collapsible disposal bag mounted on and in a container;

FIG. 15 is a cutaway cross sectional view of the access member and upper edge of the container of FIG. 14 showing the disposable collapsible bag attached to the outer edge portion of the access member;

FIG. 16 shows a cross section of a shipping box in which access members and collapsible bags of FIG. 14 may be placed in a compact stack for shipping;

DETAILED DESCRIPTION OF THE INVENTION

Figures 1, 2:
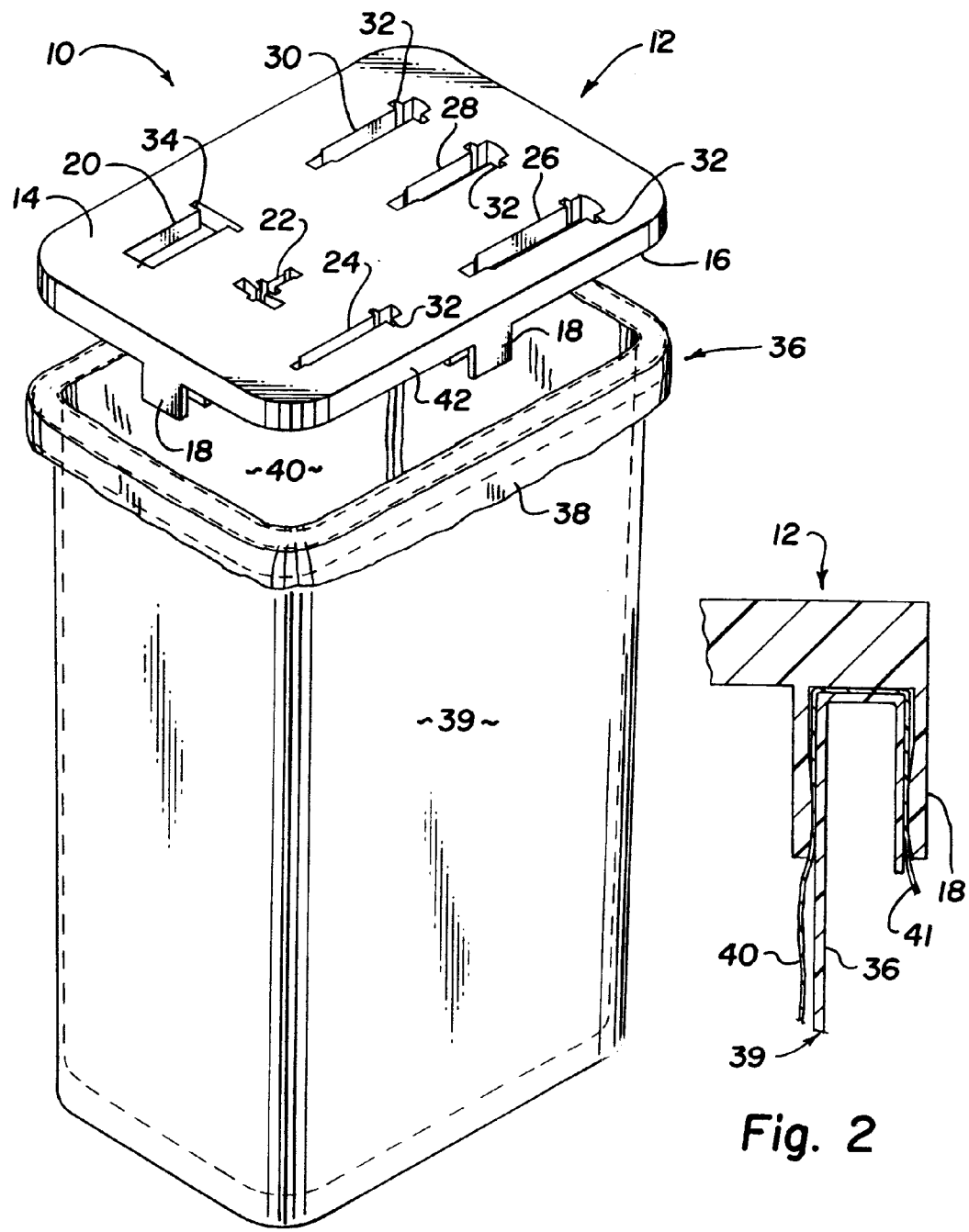
FIG. 1 is a perspective view of a disposal container lined with a removable plastic disposal bag having a clip-on access with a plurality of shaped openings which conform to the profile of different medical devices in the safe condition.
FIG. 2 is a partially cutaway cross section through a clip depending from the access member and the upper edge of the container of FIG. 1.

In the description that follows, like parts will be given the same reference numeral in so far as possible.

One version of a safety sharps bagging apparatus generally referred to as apparatus 10, is illustrated in FIGS. 1 and 2. In FIG. 1 a access member generally referred to by the reference numeral 12 is provided with a plurality of conforming openings which conform to the profile of a medical device in its safe condition. Access member 12 has an upper surface 14 and a lower surface 16 which is illustrated as a planar structure having a plurality of flexible clips 18 depending from lower surface 16. It could also be nonplanar.

Access member 12 is provided with a conforming opening 20 for a blood sampler housing, a conforming opening 22 for a winged intravenous catheter device, and conforming openings 24, 26, 28 and 30 for syringes having the same general outline shape profile but having different sizes and volumetric capacities. The term conforming opening is intended to mean an opening that has the profile of the medical device in question in its safe (retracted) condition. While the conforming opening has the shape of the safe medical device, it is slightly larger to allow clearance so that the medical device having that profile can easily pass in its safe position through the conforming opening. In its unsafe condition, the medical device is non-conforming. Although the conforming opening could be selected to require a certain angular or rotated orientation for insertion, it is preferred that the conforming opening allow the correct medical device to pass through regardless of which way it is rotationally oriented. For example, syringes commonly have a barrel portion with finger grips extending from opposite sides. These finger grips are accommodated by slots 32 which will receive the finger grips. Other devices, such as a blood sampler 20, may have a circular rim which is accommodated by a slot 34. It is expected that access member 12 will be provided with only one or more than one of the conforming openings, depending on the needs. Certain medical facilities, such as health labs, may employ only a single type of medical device and hence need only a single conforming opening in a access member of a disposal unit.

Although there are other alternatives, access member 12 may be clipped on to the upper edge portion 36 of a plastic container 39 in the nature of a waste basket having a flexible plastic disposal bag 40 removably positioned inside container 39 in the manner commonly done with plastic kitchen bags in the home. Upper edge portion 38 of bag 40 overlaps the folded over upper edge 36 of container 39 and is held by clips 18 of access member 12 as shown in FIG. 2. In this embodiment, the access member can be removed by pulling it off container 36 so that medical devices collected in disposal bag 40 can be removed with the bag. Its top is sealed with tape or secure ties in preparation for disposal of the bag and contents in an incinerator. The container, on the other hand, remains in its location of use and does not require incineration. It is reused by placing another disposal bag 40 inside, folding over the edge and replacing access member 12. It is also within the contemplation of the invention that access member 12 can be used without the disposable bag on a sharps container. This is not preferred, but can reduce the chance of having to deal with any unsafe medical devices in the disposal handling process where despite the use of conventional sharps containers, there have been needle sticks.

It can be seen that all of the medical devices depicted in FIG. 1 are retractable medical devices having an extended needle which is extended from the front of the device. The access member preferably has an appreciable thickness 42 selected to make it difficult or impossible for a unsafe medical device with the needle part extended to pass through the conforming opening intended for it. An unsafe device will bind in or on the edges of the opening. It is equally understood that if multiple openings are provided, someone could drop a winged IV catheter profile 22, for example, through the conforming opening 20 for the blood sampler or through one of the larger conforming openings 24–30 for a syringe. In this sense, neither this nor any other disposal device is 100% foolproof or sabotage proof but the present invention takes advantage of powerful psychological factors which will greatly reduce the risk of unintended disposal of unsafe devices. Surveys have shown that medical devices such as shown in U.S. Pat. Nos. 5,578,011 and 5,810,775 of the present inventor, are already retracted before disposal around 99% of the time. These patents are incorporated by reference. The present invention attacks the other roughly 1% of unsafe disposals so that for the first time bagging becomes a viable alternative. Nurses and other medical providers have a natural tendency to and receive a satisfaction from matching the device they are using with the proper conforming opening for that device. It is a natural human tendency. The access member therefore serves as an important training tool and a reminder which after a few uses becomes second nature to them. Assurance that only safe medical devices are collected in the bag is expected to closely approach 100% compliance.

Figure 3:
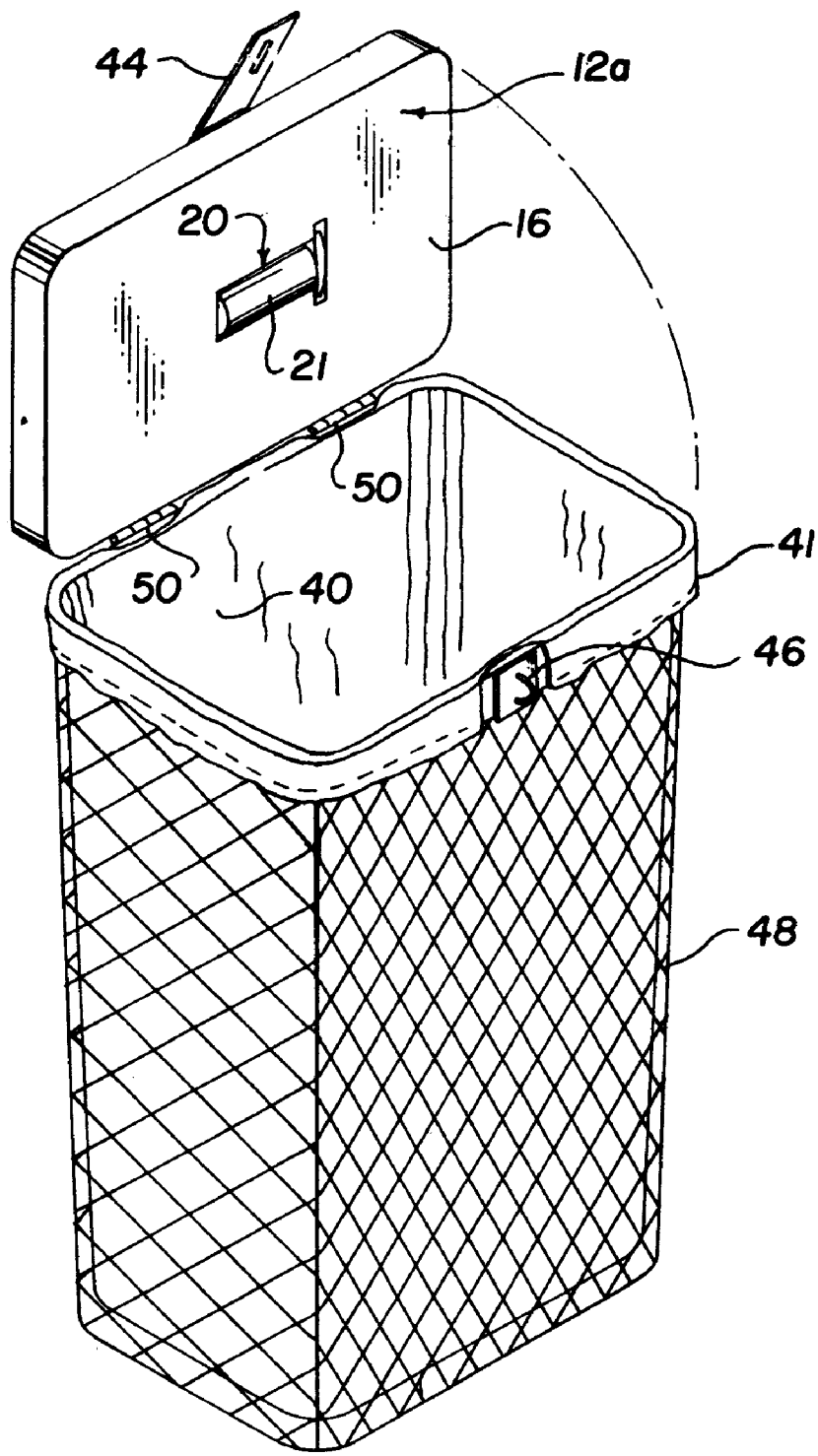
FIG. 3 is a perspective view of an alternate wire mesh container lined with a plastic disposal bag and provided with a hinged access member and a locking mechanism.

FIG. 3 illustrates a locking configuration for a access member 12a having a conforming opening 20 for a blood sampler 21, seen partially extending through opening 20. Access member 12a includes a latch 44 and hasp 46 which can be used to lock the access member onto the upper rim of a wire framed disposal container 48. A plastic disposal bag 40 is placed into container 48 with its upper edge portion 41 draped over the outer edge of wire basket 48 in a manner similar to FIG. 1. Hinges 50 complete the attachment of access member 12a to the upper edge of container 48. Such a disposal apparatus is useful where there is a fear that someone may try to retrieve or reuse discarded medical devices.

Figure 4:
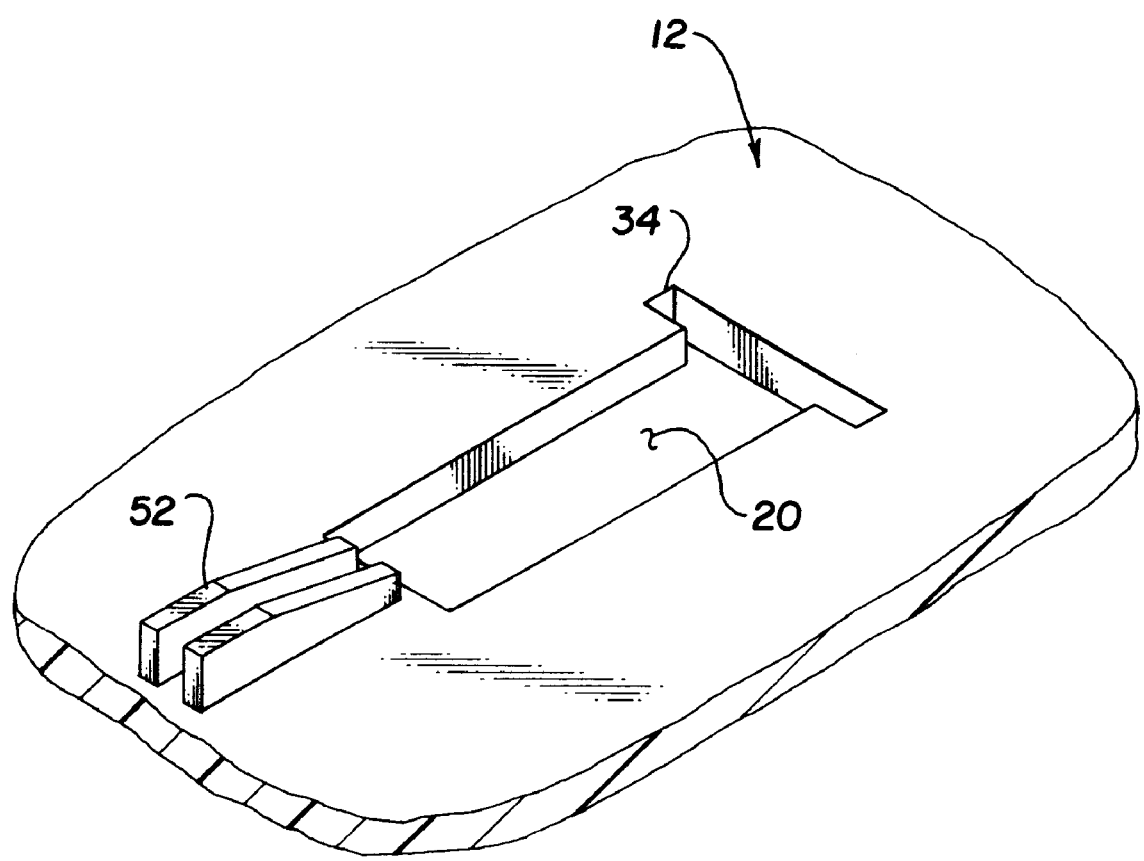
FIG. 4 is a cutaway perspective view of a access member usable with a container such as those shown in the other Figures, having a conforming opening with the profile of a blood collector housing in the safe condition and a needle guard.

FIG. 4 illustrates a conforming opening 20 which includes a back end portion having a "T"-shaped slot 34. The upper surface is provided with a needle guard 52 comprising a pair of upright spaced apart walls which partially enclose an extended needle if someone puts an unsafe blood sampler (nonconforming) into the conforming opening 20. Needle guard 52 reduces the risk that the handler will be pricked by the extended needle.

Figure 5:
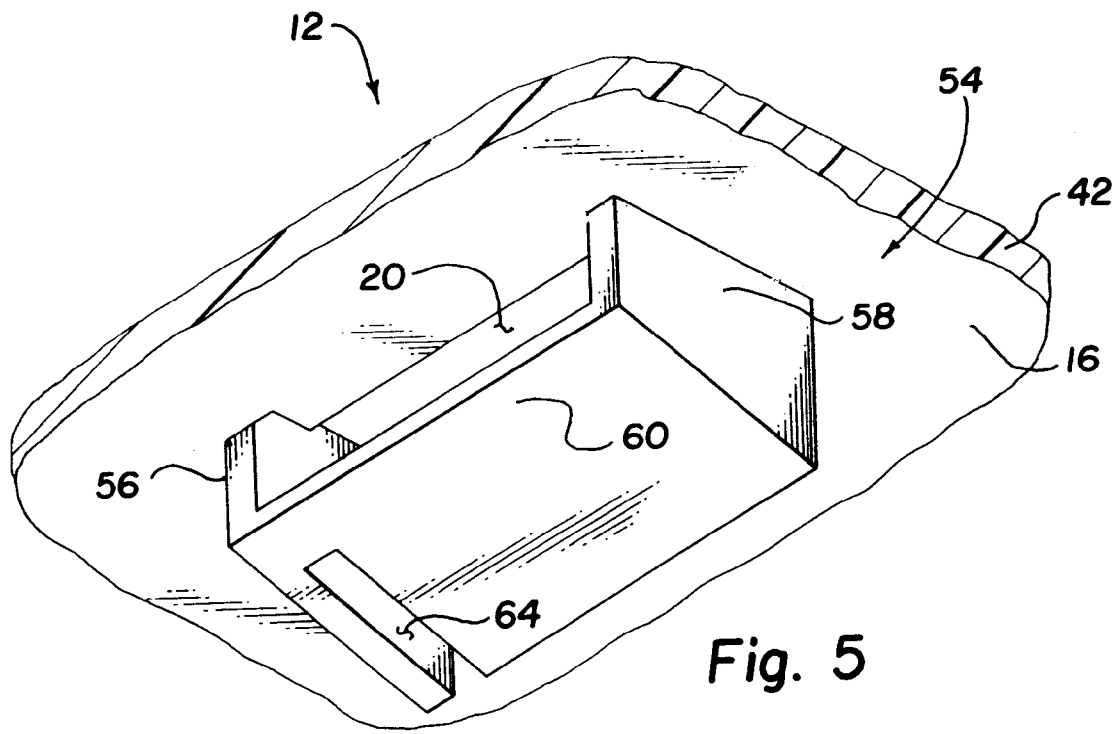
FIG. 5 is a rear perspective view of a safety shield below the conforming opening of a access member like FIG. 4, to insure that an unsafe medical device cannot pass through the opening.
Figure 6:
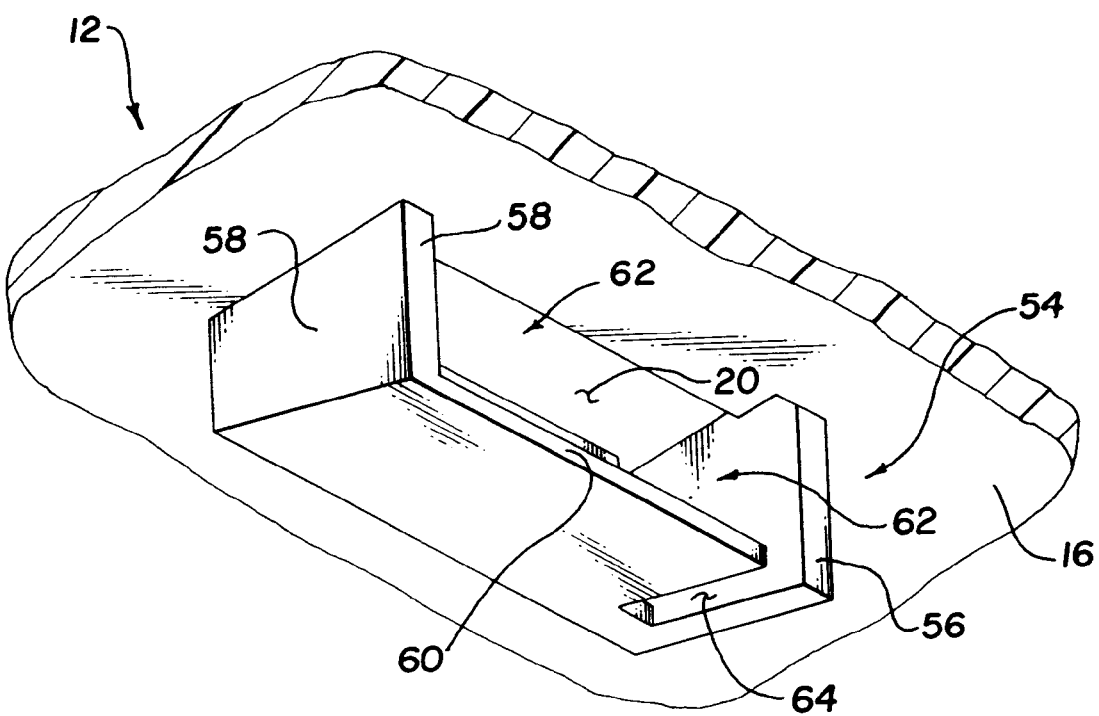
FIG. 6 is a front perspective view of the safety shield of FIG. 5.

FIGS. 5 and 6 provide two views of a safety shield 54 spaced under a conforming opening 20 in a access member 12. Safety shield 54 depends from undersurface 16 of access member 12 and may be employed in the same way under a conforming opening for a retractable syringe, other retractable device or other needle bearing safety medical device as well. The safety shield includes opposed barriers 56, 58 which support a shelf 60 directly under the conforming opening, such as conforming opening 20. Opposed barriers 56 and 58 are on opposite sides of a conforming opening, and may be employed with or without shelf 60 to prevent movement in the long direction of the conforming opening of an unsafe syringe inadvertently placed therein. Safety shield 54 generally has a "U"-shape in cross section and includes a discharge opening 62 and a corresponding opening 64 in the form of a slot or partial slot which lies directly under the "T"-shaped slot 34 or equivalent as seen in FIG. 4. Shelf 60 is preferably tilted downwardly toward discharge opening 62. Since the retractable medical devices are frequently cylindrical in shape, the tilted shelf 60 together with the opening 64 facilitate rolling of a medical device on the shelf toward discharge opening 62. The use of the safety shield increases the probability that only a safe conforming safe device can pass through the conforming opening. The access member can therefore be made from thinner material for a cost and material savings.

Figure 7:
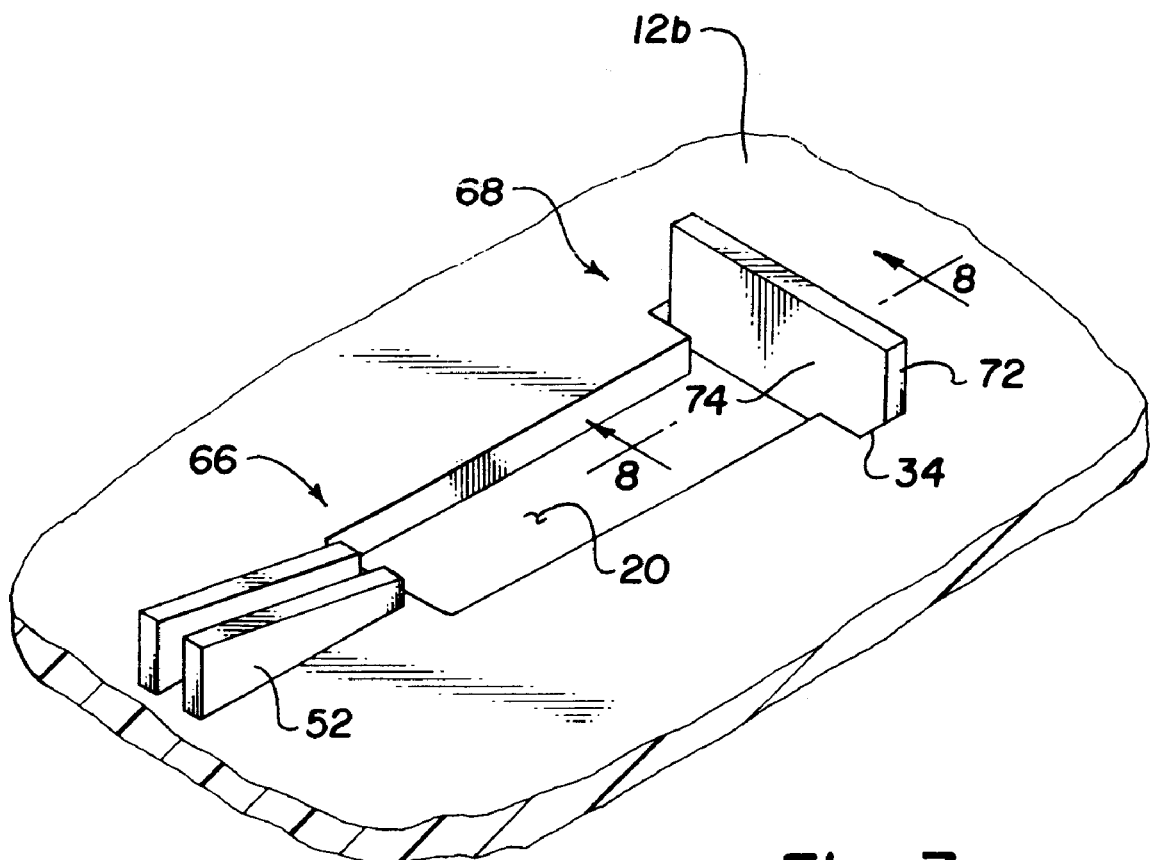
FIG. 7 is a modified access member of FIG. 4 wherein a upstanding wall behind the slotted portion of the conforming opening comprises a means for activation of a retraction mechanism.
Figure 8:
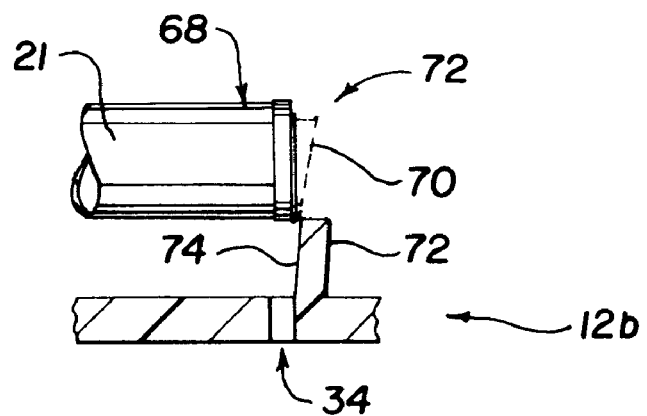
FIG. 8 is a partial cutaway side elevation of the wall of FIG. 7 shown encountering the activation structure of a blood sampler to cause retraction.

FIGS. 7 and 8 illustrate another aspect of the invention. Access member 12b is identical to the access member 12 in FIG. 4 in most respects. Each of the exemplary retractable medical devices may be considered as having a front end portion 66 from which a needle is extended and a back end portion 68 having a structure which operates the retraction mechanism. The conforming opening 20 has what we will refer to as the front end portion 66 and back end portion 68. In this case, a blood sampler housing has a cap 70 which operates the retraction structure in the blood sampler when cap 70 is fully closed. FIG. 8 shows a side view of an incompletely retracted blood sampler 21 being pushed downwardly toward opening 20 of access member 12b. Back end portion 68 of opening 20 includes a pressing wall 72 having a sharply angled surface 74 which presses on the activation structure to retract the medical device by means of cap 70. We may refer to this as a back end portion of the conforming opening which may also take the form of FIGS. 9–12.

Figure 9:
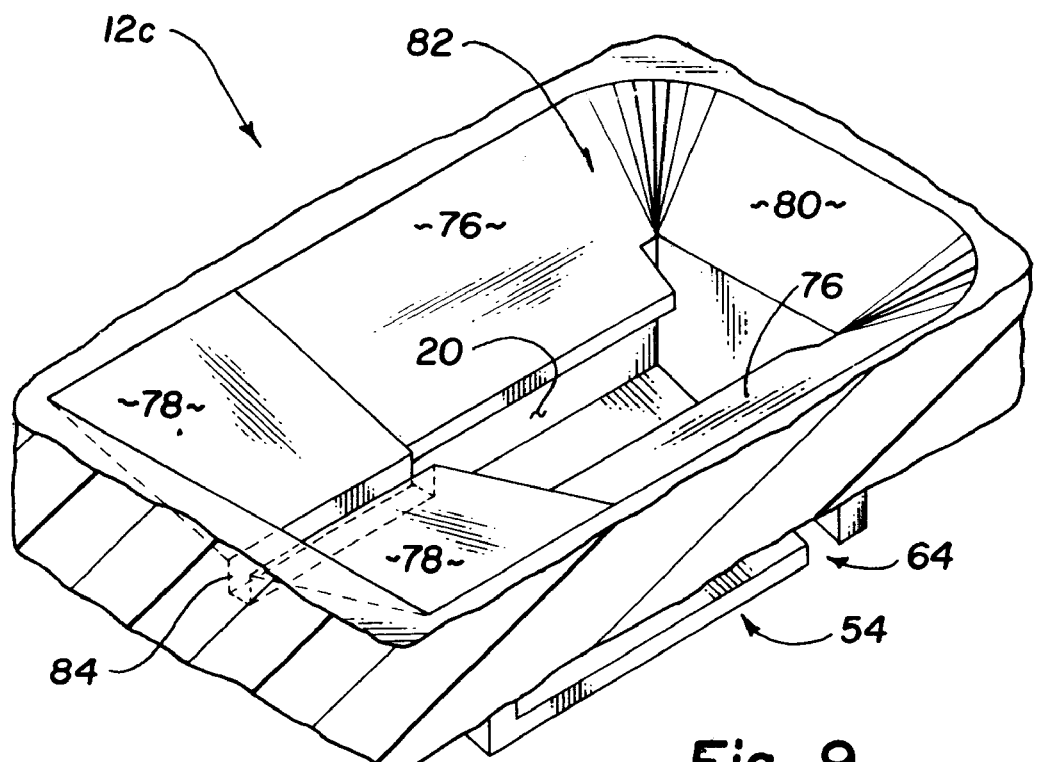
FIG. 9 is a cutaway perspective view of a access member with a conforming opening being surrounded by sloping surfaces to center a medical device over a conforming opening above a safety shield.

In FIG. 9, access member 12c has sloping surfaces 76, 78 and 80 leading to a conforming opening 20 of access member 12c. This creates a centering well 82 which tends to cause a retracted medical device with the conforming profile to automatically center itself in relation to conforming opening 20. A separation between sloping surfaces 78 creates a needle slot 84 which serves a protective friction as a needle guard in the event a device with an unretracted needle is attempted to be inserted by means of well 82 into and through conforming opening 20. The access member of FIG. 9 further includes in combination a safety shield 54 as described in FIGS. 5 and 6.

Figure 10:
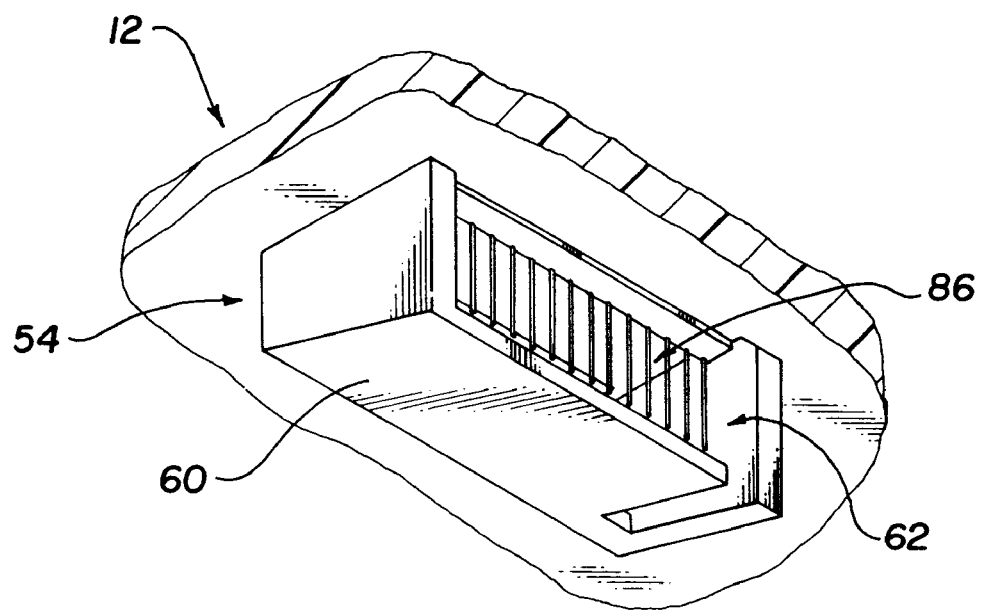
FIG. 10 is a perspective view of the front of a safety shield of any of the other Figures, including a flexible member which prevents medical devices that have passed through the conforming opening from passing back through from the opposite direction.

FIG. 10 illustrates a modification of the safety shield 54 in which a flexible member or a series of flexible members 86 is placed to flexibly block the discharge opening 62 so that a medical device which has been deposited in a disposal bag after going through a conforming opening will not fall out of the access member and bag if inverted. It is to be understood that the flexible member could be plastic fingers, bristles, spring members, etc. and could be placed in any particular location which prevents previously collected medical devices in a container under the access member from failing back out of the conforming opening without interfering with insertion of safe medical devices through a conforming opening.

Figure 11:
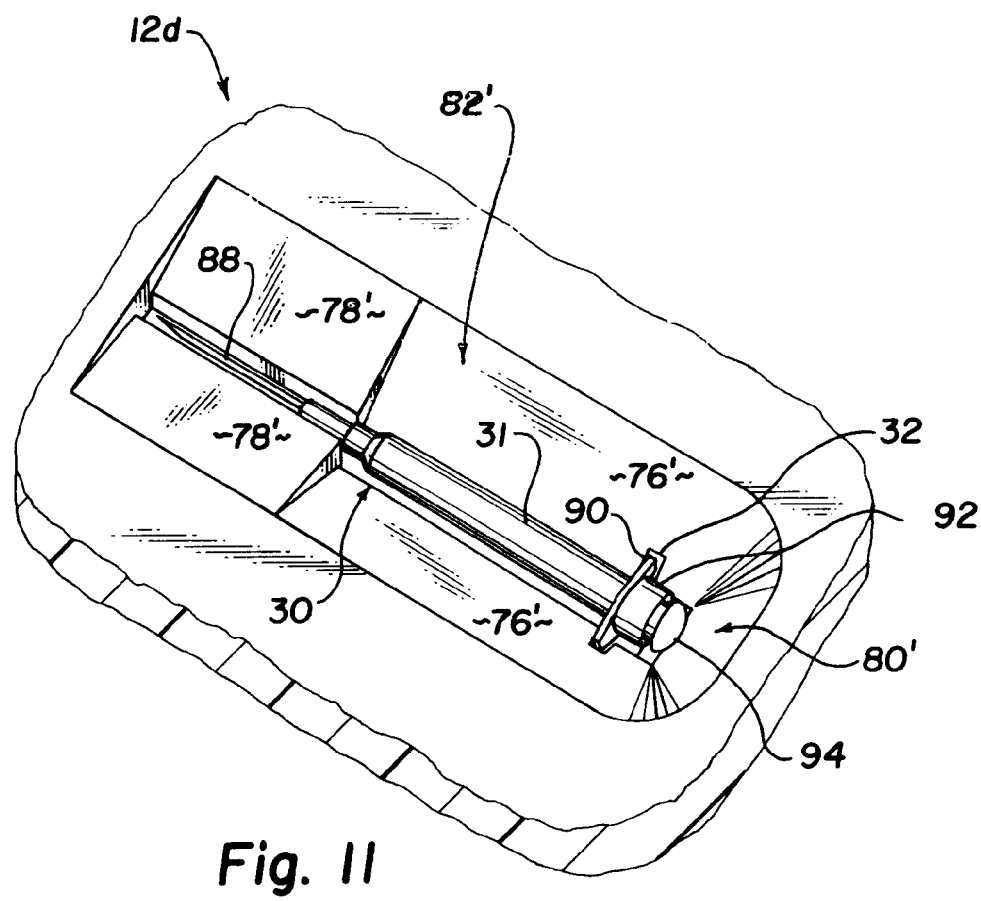
FIG. 11 is a access member having sloping sides which create a well having the shape of a retractable syringe therein.
Figure 12:
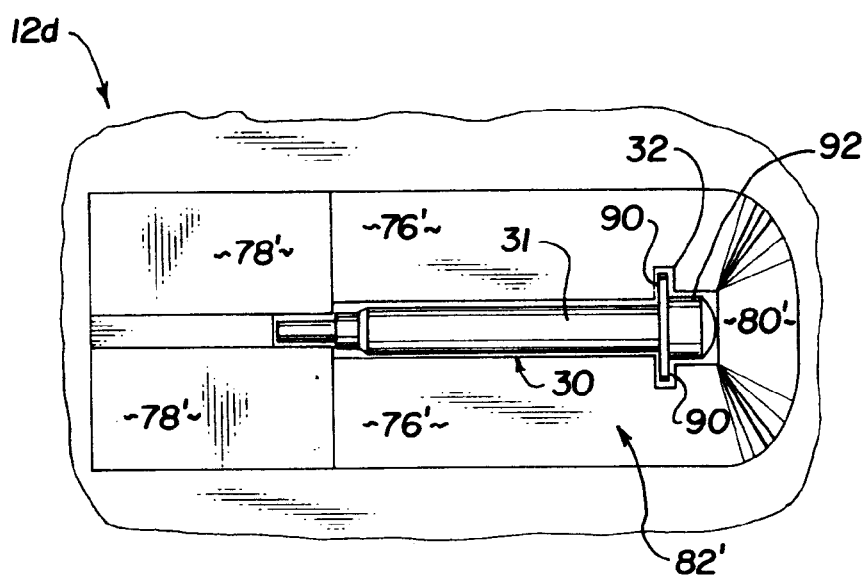
FIG. 12 is a plan view of the access member of FIG. 11 showing the outline of the conforming opening receiving the retracted syringe of FIG. 12.
Figure 13:
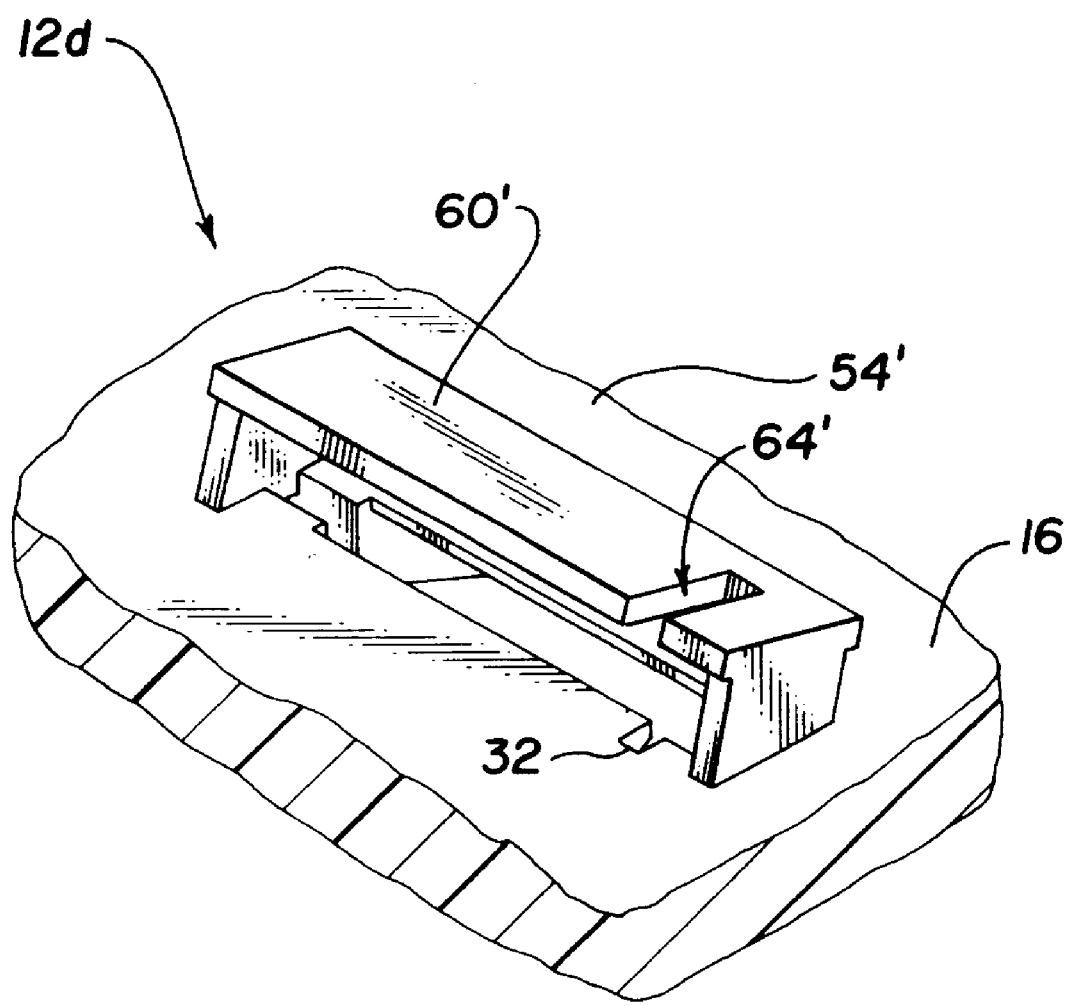
FIG. 13 is a cutaway perspective view of the underside of FIG. 11 or 12 showing the front side of a safety shield in combination with a conforming opening for a syringe.

FIGS. 11 and 12 are similar to the access member of FIG. 9 except that access member 12d in FIGS. 11 and 12 has a conforming opening for a retracted syringe instead of the body of a blood sampling device. A conforming opening 30, for example, is shown with a syringe 31. In FIG. 11 an extended retractable part comprising a needle 88 is shown extended from the forward part of the syringe in the unretracted unsafe condition of the syringe. In FIG. 12 the retracted safe condition of the syringe is seen. As in FIG. 9, sloping surfaces 76', 78' and 80' mirror those surfaces of FIG. 9 to create a centering well 82'. The "T"-slot 32 is adapted to accommodate entry of a radially enlarged part of 90 of syringe 31 in the form of finger grips which are usually found on syringes. Conforming opening 30 also includes a widened portion to accommodate a widened back end part 92 of the profile of syringe 31. As seen in FIG. 11, the syringe includes an activation structure 94 in the form of the thumb cap on the plunger which is visibly separated from widened back end part 92 in FIG. 11. If syringe 31 is pushed down to try to push it through the opening, the sharply angled surface 80' serves as a camming surface which causes the activation structure to retract the syringe which can then fall through the conforming opening 30 into a disposal bag below. FIG. 13 shows a slight modification of safety shield 54 to accommodate the slightly different shape of the conforming opening of the syringe. Here the slightly modified safety shield 54' differs in that the corresponding opening 64' is moved back slightly to fall directly below the "T"-slot 32 of FIG. 12 so that the syringe can roll freely from the tilted shelf 60'.

FIGS. 14–16 illustrate the combination of the access member 12e having a single conforming opening 20 in combination with a collapsible flexible disposal bag 96. Disposal bag 96 is made of flexible material which could include fabric, fiber or treated fabric or fiber products or preferably plastic, or a combination thereof which are impervious to fluid. Container 39 has rigid or semi-rigid sides which enclose the interior and the removable plastic disposal bag inside which collects safe medical devices that enter the interior of the container through access member 20. Collapsible disposal bag 96 has an upper edge portion 98 forming its mouth which is secured to a access member, such as access member 12e. This permits the access member and bag to be removed and replaced as a unit. It also enjoys the special advantage shown in FIG. 16 in which a plurality of units which comprise the combination of the access member and the collapsible disposal bag are stacked with the disposal bag collapsed in a box 100 for shipping and storage. In this particular embodiment, the access member and bag will be dealt with as a unit including incineration after the disposal bag is filled with collected retracted medical devices.

Figure 17:
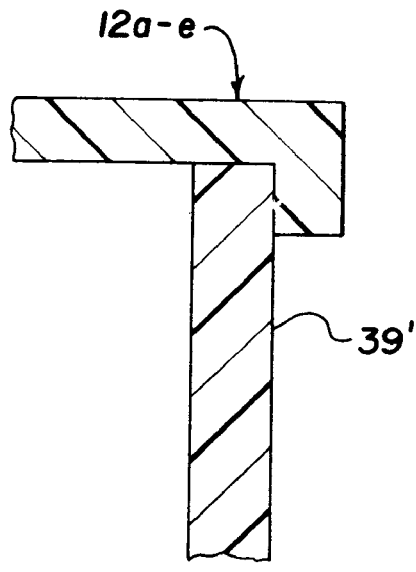
FIG. 17 is a partial cross section of the edge of a container and a access member.
Figure 18:
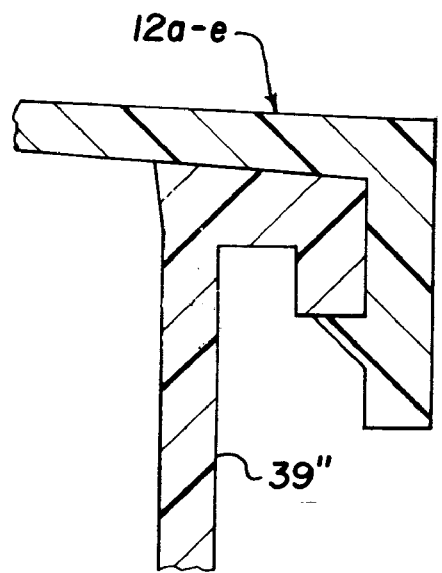
FIG. 18 is a partial cross section of a locking version of a access member and the upper edge of a container.

Although the upper edge portion 98 of the bag is shown secured to the outer edge portion of access member 12e, it could be secured at any suitable location since the mouth of the bag simply has to circumscribe the conforming opening. Therefore, the place where the bag is secured to the access member could be radially inward from the mouth of container 39. This would facilitate the use of different ways to support the access members 12a–e onto containers 39, 39' or 39" shown in FIGS. 17 and 18. A further means of removably supporting the access member on a container would include the container having a shelf on which the access member is recessed and supported. It may also be noted that the disposal containers can be fastened to the access member by the use of adhesive tape, heat sealing, stitching, bolting or clamping. In a more economical version of FIGS. 14–16, the access member can be formed of a material such as fiberboard or even stiff cardboard instead of the preferred plastic, much in the manner of a disposable vacuum cleaner bag which has an inflexible or relatively inflexible panel with an opening, attached to a collapsible bag.

Figure 19:
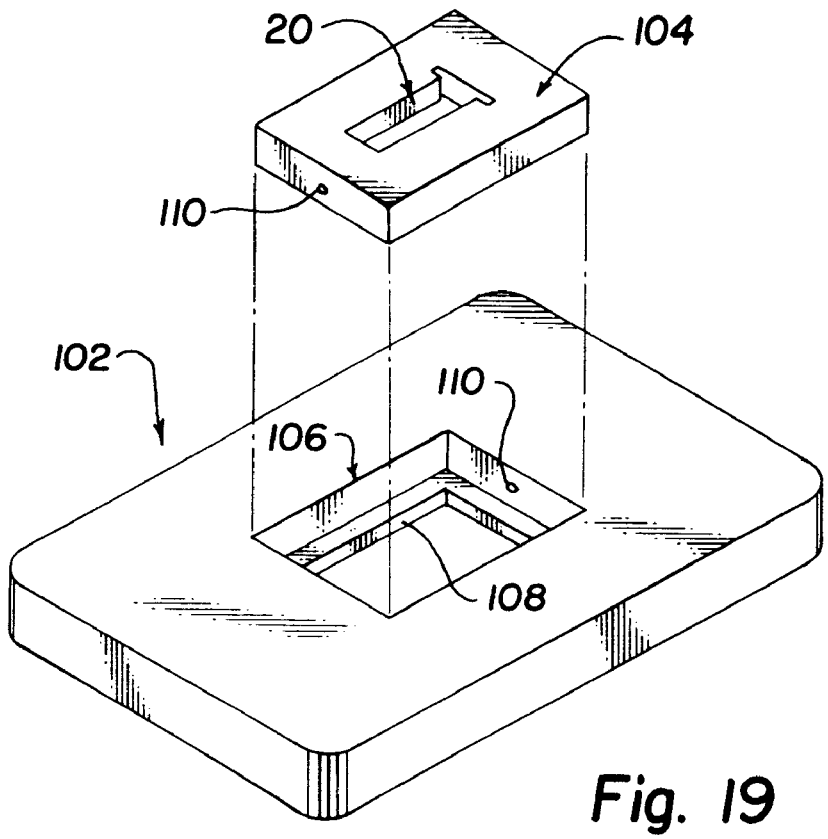
FIG. 19 is a perspective view of a universal access member having an opening to receive an insert having a desired conforming opening.

FIG. 19 discloses a universal access member 102 which has the same attributes as the access members previously disclosed except that the conforming opening, such as conforming opening 20, is contained in an insert 104. Insert 104 is shown in a rectangular configuration but could be circular, octagonal, etc. Other inserts 104 could be provided with openings for syringes, winged IV catheters, etc. for places where those devices are used. It is also contemplated to have a access member 102 which contains a plurality of inserts in a manner to be described. Access member 102 includes an opening 106 which has a supporting shelf 108 and detents 110 or other conventional holding devices which allow insert 104 to be removably held in the opening 106 of access member 102. This combination has the advantage that molds for a single access member can be provided that can accommodate a plurality of inserts each having a different conforming opening in them and it allows changing from one insert to another.

Although the present invention has been described in detail with reference to only the presently preferred embodiments, it will be appreciated by those of ordinary skill in the art that various modifications can be made without departing from the invention.

I claim:

1. An access member for a sharps disposal container for safe disposal of a medical device having a sharp needle or blade, wherein the profile of the medical device in its safe condition is different than the profile of the medical device in its unsafe condition, comprising:

an access member adapted for use with a disposal container for sharps;

the access member having a conforming opening therein conforming to the profile of the medical device in its safe condition; and whereby the medical device will pass through the conforming opening in the access member only in the safe condition of the medical device.

2. The access member of claim 1 further including a disposal bag in combination with the access member for collecting medical devices in the safe condition, which pass through the conforming opening.

3. The access member of claim 1 wherein said access member has a one or more additional conforming openings including at least one additional conforming opening different than said conforming opening and conforming to the profile of an additional medical device in its safe condition which is non-conforming to the profile of the additional device in its unsafe condition.

4. The access member of claim 2 wherein said access member has a one or more additional conforming openings including at least one additional conforming opening different than said conforming opening and conforming to the profile of an additional medical device in its safe condition which is non-conforming to the profile of the additional device in its unsafe condition.

5. The access member of claim 1 wherein the access member has an upper surface and a lower surface separated by a thickness and includes a safety shield spaced under the conforming opening, depending from the access member, said safety shield preventing passage of a medical device with a conforming profile from passing through the conforming opening in any orientation, unless it is in its safe condition.

6. The access member of claim 5 wherein the access member includes a flexible member associated with the conforming opening which prevents medical devices that have passed through the conforming opening in one direction from passing through the conforming opening again from the opposite direction.

7. The access member of claim 5 wherein the safety shield is positioned to cooperate with the edges of the conforming opening to prevent medical devices when in their unsafe condition from passing therethrough.

8. The access member of claim 2 wherein the disposal bag has an upper edge portion comprising a mouth secured to the outer edge portion of the access member.

9. The apparatus of claim 8 further including a shipping box wherein a plurality of access member and bag combinations are stacked one over the other with the bags collapsed.

10. The access member of claim 2 wherein the access member includes a flexible member flexibly blocking the conforming opening so that a medical device which has been deposited in the disposal bag will not fall out if the access member and bag are inverted.

11. An access member for a sharps disposal container for safe disposal of a medical device having a sham needle or blade, wherein the profile of the medical device in its safe condition is different than the profile of the medical device in its unsafe condition, comprising:

an access member adapted for use with a disposal container for sharps;

the access member having a conforming opening therein conforming to the profile of the medical device in its safe condition;

the access member having an upper surface and a lower surface separated by a thickness and includes a safety shield spaced under the conforming opening, depending from the access member said safety shield preventing passage of a medical device with a conforming profile from passing through the conforming opening in any orientation, unless it is in its safe condition; and the conforming opening further including a "T"-shaped slot for receiving a radially enlarged part of a medical device and the safety shield includes a corresponding opening spaced below said slot to facilitate rolling movement of a medical device which enters the safety shield.

12. An access member for a sharps disposal container for safe disposal of a medical device having a sharp needle or blade, wherein the profile of the medical device in its safe condition is different than the profile of the medical device in its unsafe condition, comprising;

an access member adapted for use with a disposal container for sharps;

the access member having a conforming opening therein conforming to the profile of the medical device in its safe condition;

wherein the access member has an upper surface and a lower surface separated by a thickness and includes a safety shield spaced under the conforming opening, depending from the access member;

wherein said safety shield comprises a shelf directly under the conforming opening and opposed barriers on opposite sides of the conforming opening; and said safety shield preventing passage of a medical device with a conforming profile from passing through the conforming opening in any orientation, unless it is in its safe condition.

13. The access member of claim 12 wherein said shelf is tilted with respect to the lower surface of the access member thereby creating a discharge opening for medical devices passing through the conforming opening.

14. The access member of claim 13 wherein the conforming opening includes a "T"-shaped slot for receiving a radially enlarged part of a medical device and the safety shield includes a corresponding opening spaced below said slot at approximately the level of the shelf to facilitate rolling of a medical device on the shelf toward the discharge opening.

15. An access member for a sharps disposal container for safe disposal of a medical device having a sharp needle or blade, wherein the profile of the medical device in its safe condition is different than the profile of the medical device in its unsafe condition, comprising;
an access member adapted for use with a disposal container for sharps;
the access member having a conforming opening therein conforming to the profile of the medical device in its safe condition;
said access member having sloping surfaces leading to the conforming opening in said access member, wherein a centering well is created which tends to cause a medical device with the conforming profile to automatically center itself in relation to the conforming opening and
whereby the medical device will pass through the conforming opening in the access member only in the safe condition of the medical device.

16. The access member of claim 15 wherein the profile of said medical device comprises a back end portion having an activation structure for a retraction mechanism and a front end having the needle and wherein the conforming opening includes a back end portion which presses the activation structure of said medical device.

17. The access member of claim 16 wherein an upright sharply sloping surface is provided in the access member at the back end portion of the conforming opening, said sharply sloping surface tending to operate the activation structure when an unretracted medical device with the conforming profile is attempted to be pushed through the conforming opening thereby causing the medical device to retract.

18. An access member for a sharps disposal container for safe disposal of a medical device having a needle, wherein the profile of the medical device in its safe condition is different than the profile of the medical device in its unsafe condition, comprising:
an access member adapted for use with a disposal container for sharps;
the access member having a conforming opening therein conforming to the profile of the medical device in its safe condition;
the access member including a needle guard ahead of the front end of the conforming opening and
whereby the retractable medical device will pass through the conforming opening in the access member only in the safe condition of the medical device.

19. An access member for a sharps disposal container for safe disposal of a medical device having a sharp needle or blade, wherein the profile of the medical device in its safe condition is different than the profile of the medical device in its unsafe condition, comprising
an access member adapted for use with a disposal container for sharps;
the access member having a conforming opening therein conforming to the profile of the medical device in its safe condition;
wherein the conforming opening is contained in an insert and the access member has an opening adapted to hold said insert thereby permitting a single access member to be used with different inserts having different conforming openings; and
whereby the retractable medical device will pass through the conforming opening in the access member only in the safe condition of the medical device.

20. The access member of claim 19 wherein another conforming opening is contained in another insert and the access member has openings adapted to hold each of said inserts.

21. The access member of claim 20 wherein said insert and said another insert have different conforming openings to conform to the profile of medical devices of different volumetric capacities or sizes in the safe condition.

22. The access member of claim 19 further including a disposal bag having a mouth comprising an upper edge portion secured to the access member radially outwardly from the opening for the insert.

23. The access member of claim 20 wherein the access member has an outer edge portion, further including a disposal bag having a mouth comprising an upper edge portion secured to the outer edge portion of the access member.

24. Apparatus for safe disposal of a medical device having a sharp needle or blade, wherein the profile of the medical device in its safe condition is different than the profile of the medical device in its unsafe condition, comprising:
a container having an open side leading into an interior for receiving and collecting used retractable medical devices;
an access member positioned over said open side through which medical devices pass to reach the interior of the container;
the access member having a conforming opening therein conforming to the profile of a medical device in its safe condition and leading into the interior of the container; and
whereby the retractable medical device will pass through the conforming opening in the access member only in the safe condition of the medical device.

25. The apparatus of claim 24 herein the access member and the container have cooperating edge portions which serve to hold the access member in position.

26. The access member of claim 24 wherein the container, has rigid or semi-rigid sides enclosing the interior and a removable disposal bag inside the container, the disposal bag being made of flexible material which collects medical devices that enter the interior of the container through the access member.

27. The access member of claim 26 wherein the disposal bag has an upper edge portion forming its mouth wherein the upper edge portion is secured to the access member whereby the bag and the access member are removed and replaced as a unit.

28. The access member of claim 27 further including a shipping box wherein a plurality of said units are stacked one over the other with the bags collapsed.

29. The access member of claim 27 wherein the access member has an outer edge portion and the upper edge portion of the bag is secured to the access member along said outer edge portion.

30. The access member of claim 26 wherein a flexible member associated with the conforming opening prevents previously collected medical devices in the container from falling back out of the conforming opening.

31. The access member of claim 24 wherein a flexible member associated with the conforming opening prevents previously collected medical devices in the container from falling back out of the conforming opening.

* * * * *

UNITED STATES PATENT AND TRADEMARK OFFICE
CERTIFICATE OF CORRECTION

PATENT NO.    : 6,474,472 B1
DATED         : November 5, 2002
INVENTOR(S)   : Thomas J. Shaw It is certified that error appears in the above-identified patent and that said Letters Patent is hereby corrected as shown below:

<u>Column 7,</u>
Line 47, replace "friction" with -- function --.

<u>Column 10,</u>
Line 20, replace "sham" with -- sharp --.

<u>Column 12,</u>
Line 38, replace "herein" with -- wherein --.
Line 41, replace "container," with -- container --.

Signed and Sealed this

Fourth Day of March, 2003

JAMES E. ROGAN
*Director of the United States Patent and Trademark Office*